United States Patent [19]

Strandberg

[11] Patent Number: 4,886,064
[45] Date of Patent: Dec. 12, 1989

[54] BODY ACTIVITY CONTROLLED HEART PACER

[75] Inventor: Hans Strandberg, Sundbyberg, Sweden

[73] Assignee: Siemens Aktiengesellschaft, Berlin and Munich, Fed. Rep. of Germany

[21] Appl. No.: 125,573

[22] Filed: Nov. 25, 1987

[51] Int. Cl.⁴ .................... A61N 1/00; H05G 00/00
[52] U.S. Cl. .......................... 128/419 PG; 128/903
[58] Field of Search ............ 128/321, 419 P, 419 PG, 128/903, 904; 364/413.03, 413.06

[56] References Cited

U.S. PATENT DOCUMENTS

| | | | |
|---|---|---|---|
| 3,241,556 | 3/1966 | Zacouto | 128/421 |
| 4,428,378 | 1/1984 | Anderson et al. | 128/419 PG |
| 4,453,162 | 6/1984 | Money et al. | 340/870.39 |
| 4,543,955 | 10/1985 | Schroeppel | 128/419 PG |
| 4,791,931 | 12/1988 | Slate | 128/419 PG |

FOREIGN PATENT DOCUMENTS

| | | | |
|---|---|---|---|
| 0089014 | 9/1983 | European Pat. Off. | 128/419 PG |
| 0191404 | 8/1986 | European Pat. Off. | 128/419 PG |

OTHER PUBLICATIONS

Sensolog 703, Physician's Manual.

*Primary Examiner*—Francis Jaworski
*Assistant Examiner*—George Manuel
*Attorney, Agent, or Firm*—Hill, Van Santen, Steadman & Simpson

[57] ABSTRACT

Body activity sensors, such as temperature, motion, respiration and/or blood oxygen sensors, are positioned in a patient's body outside the pacer capsule. These sensors wirelessly transmit body activity signals, which are processed by circuitry in the heart pacer, such that a stimulation pulse generator within the pacer capsule is controlled by the body activity signals. Preferably, the transmission between the sensors and the capsule is two-way, thereby allowing the sensors to receive control signals for altering the sensor characteristics.

8 Claims, 2 Drawing Sheets

BODY ACTIVITY CONTROLLED HEART PACER

BACKGROUND OF THE INVENTION

1. Field of the Invention

The present invention relates to a body activity controlled heart pacer provided for being positioned at or in the body of a patient.

2. Description of the Prior Art

European patent application No. 0 089 014 (Plicchi et al.) describes a body activity controlled heart pacer, which utilizes a respiration signal, that is derived from a body impedance measurement, as a body activity signal. The electrodes for measuring the body impedance are positioned in a body location which is different from the heart pacer capsule location. Furthermore, the electrodes are connected by leads (wire) to stimulation pulse rate controlling means inside the pacer capsule. A lead connection is, however, technically too complicated, especially if a plurality of sensors is employed.

A similar rate adaptive pacer is depicted in U.S. Pat. No. 4,428,378 (Anderson et al.). This pacer utilizes a motion sensor instead of an impedance (respiration) sensor to measure body activity. The motion sensor is inserted in the pacer capsule and again connected by wire to the remaining pacer components inside the pacer capsule. External body activity connection leads are not required in this case; the pacer capsule nevertheless becomes more voluminous.

Finally, another body activity controlled pacer is being marketed by Siemens-Elema under the name SENSOLOG 703 (See, for example, Siemens brochure A91003-M3372-L943-01-7600). A piezoelectric sensor is also used in this case. The signals are, however, processed differently from Anderson et al.

SUMMARY OF THE INVENTION

It is an object of the present invention to provide a pacer capsule for a body activity controlled pacer, which requires as little volume as possible, even when a plurality of sensors are used. It is another object of the invention to provide a body activity controlled pacer, which utilizes no external leads for connecting one or more sensors with a pacer capsule. It is still a further object of the present invention to provide a body activity controlled pacer, which may be located in or at a body of a patient, such that body activity may be optimally registered.

According to the present invention a body activity controlled heart pacer is provided for being positioned at or in the body of a patient, which comprises:

(a) a first device including:
 (a1) pulse generating means for generating stimulation pulses at a basic rate;
 (a2) controlling means for controlling said pulse generating means such that said basic rate is varied as a function of at least one body activity signal; and
(b) a second device including means for sensing body activity and for generating said body activity signal; wherein said first device is provided for being positioned in or at a first body location; and wherein said second device is provided for being positioned in or at a second body location; and wherein said means for sensing body activity comprises means for wirelessly transmitting said body activity signal; and wherein said controlling means comprises means for wirelessly receiving said body activity signal.

According to the invention, the body activity sensors are disposed in a device, which is separate from the pacer capsule. The pacer can again be dimensioned as small as possible. Contrary to conventional devices, however, a wire connection is no longer necessary. Under the circumstances, the sensors can be positioned in such body locations which are optimally suited for measuring body activity, while the small pacer capsule sits in its usual location. If a plurality of body activity sensors is employed for measuring a variety of body activity parameters (e.g. such as temperature, respiration, motion, blood oxygen), each sensor can be positioned in a separate device and in a location which is most suitable for measuring the corresponding parameter.

The foregoing and other objects, features and advantages of the invention will be apparent from the following more particular description of a preferred embodiment of the invention, as illustrated in the accompanying drawings.

DETAILED DESCRIPTION OF THE PREFERRED EMBODIMENTS

Figure 1:
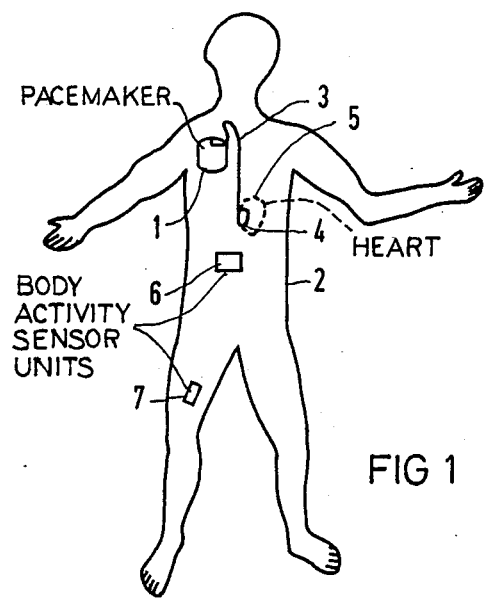
FIG. 1 illustrates the positioning of a pacer capsule including the pacing lead and two body activity sensors at different locations within the body of a patient.

In FIG. 1 a pacer capsule 1 is shown implanted in the body 2 of a patient. An ordinary pacing lead 3, connected to the pacer capsule 1, is inserted with its pacing electrode 4 in the heart 5 of the patient. A first sensor unit 6 is positioned at a first location (e.g. under the ribs). A second sensor unit 7 is implanted beneath the skin of one of the patient's thighs. The first sensor unit 6 measures, for example, body temperature, while the second unit 7 measures body motion.

Figure 2:
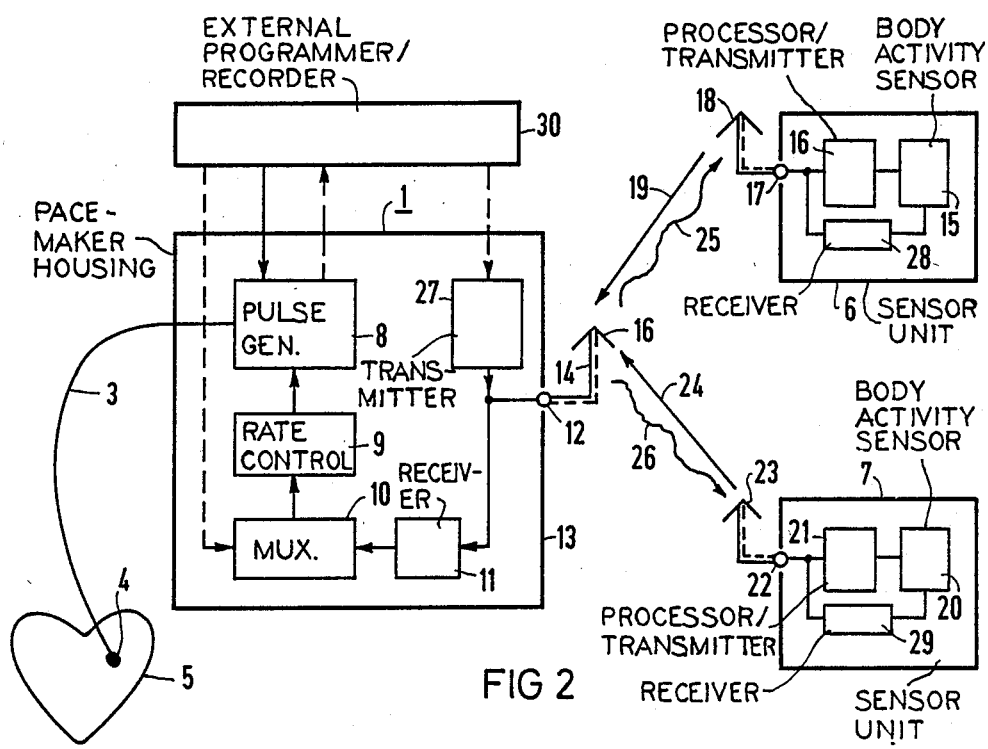
FIG. 2 is a schematic block diagram of a body activity controlled heart pacer in accordance with FIG. 1, utilizing the principles of the present invention.

As shown in FIG. 2, the pacer capsule 1 comprises a basic rate stimulation pulse generator 8, a stimulation rate controlling unit 9, a multiplexer 10, and a receiving unit 11. The receiving unit 11 is connected with a signal input 12, that is electrically insulated from the surface 13 of the pacer capsule 1. The signal input 12 serves as a receiving antenna 14 (as indicated by broken lines).

The first sensor unit 6 comprises a body activity sensor 15, which measures, for example, body temperature and thereupon supplies a body activity signal. The first sensor unit 6 also comprises a body activity signal processing and transmitting unit 16. A signal output for the transmitted signal is generally designated with reference number 17. This signal output 17 serves as a transmitting antenna 18, as indicated by broken lines. The transmitting signal wirelessly transmitted from the signal output 17 of the first sensor unit 6 to the signal input 12 of the pacer capsule 1 is referenced by 19. Correspondingly, the second sensor unit 7 comprises a body activity sensor 20, which measures, for example, body motion and thereupon supplies a second body activity signal. The second sensor unit 7 also comprises a body activity signal processing and transmitting unit 21. A signal output 22 serves as a transmitting antenna 23, as again indicated by broken lines. The wirelessly transmitted signal from the signal output 22 of the second sensor unit 7 to the signal input 12 of the pacer capsule 1 is referenced by 24.

The operation is as follows: The signals 19 and 24 transmitted from the first and second sensor units 6, 7 pass through body tissue and are received by the receiving unit 11 inside the pacer capsule 1 via signal input 12. Multiplexer 10 multiplexes the amplified output signal of the receiving unit 11 and supplies its output signal to the stimulation rate controlling unit 9. The stimulation rate controlling unit 9 controls the basic rate stimulation pulse generator 8 by varying the basic rate as a function of the output signals of the first and/or second sensor units 6, 7.

The signal transfer can be one-way from the first and second sensor units 6, 7 to the pacer capsule 1. Preferably however, this transfer is two-way, as indicated by wavy arrows 25, 26. In this case, information (e.g. control data) can be transmitted from the pacer capsule 1 through antenna 14 to antennas 18 and 23 of the respective first and second sensor units 6, 7. The antenna 14 then works as a transmitting antenna and the antennas 18 and 23 of the first and second sensor units 6, 7 function as receiving antennas. For this purpose, the pacer capsule 1 also includes a transmitting unit 27. The body activity signal processing and transmitting units 16, 21 of the first and second sensor units 6, 7 are respectively supplemented by receiver units 28, 29.

The additional information transmitted from the pacer capsule 1 to the first and second sensor units 6, 7 can be control signals, used for switching the first and second sensor units 6, 7 on and off, or for altering other parameters of these units. For this purpose, the transmitting unit 27 inside the pacer capsule 1 can be controlled by an external programmer and recorder unit 30. The external programmer and recorder unit 30 may also program and record further parameters of the components housed in pacer capsule 1 (e.g. basic rate stimulation pulse generator 8 and/or multiplexer 10).

Figure 3:
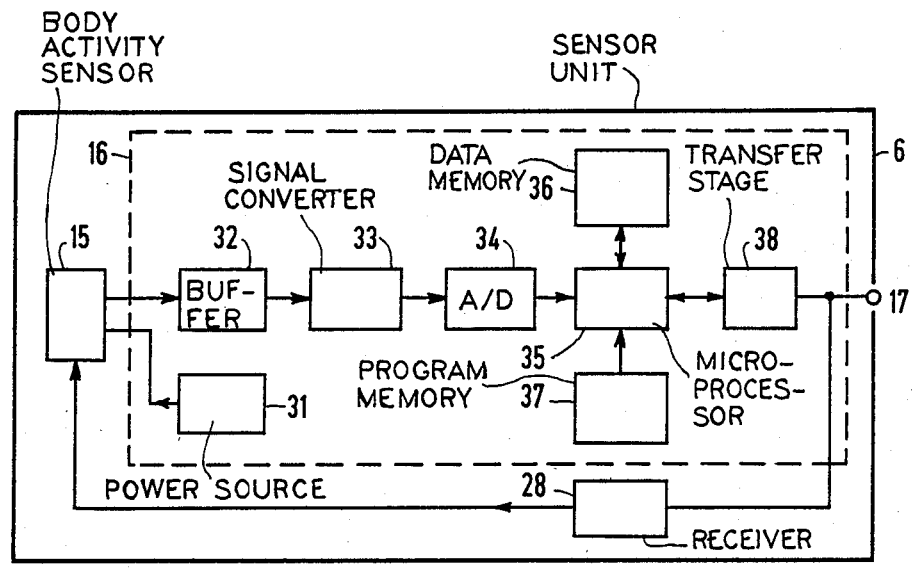
FIG. 3 is a detailed schematic block diagram of a sensor unit of FIG. 2.

FIG. 3 shows a sensor unit, for example body temperature sensor unit 6, in a detailed schematic block diagram. As can be seen from this Figure, the body activity signal processing and transmitting unit 16 comprises a power source 31 (e.g. battery), a buffer circuitry 32, a signal converter 33, an analog to digital converter 34, a microprocessor 35, including a data memory 36 and a program memory 37, and transfer electronics 38.

Having thus described the invention with particular reference to the preferred forms thereof, it will be obvious to those skilled in the art to which the invention pertains, after understanding the invention, that various changes and modifications may be made therein without departing from the spirit and scope of the invention as defined by the claims apended hereto.

What is claimed is:

1. A body activity-controlled heart pacing system comprising:
   at least one body activity sensor unit including means for sensing body activity and for generating a body activity signal corresponding thereto, and means for wirelessly transmitting said body activity signal, said at least one body activity sensor unit adapted to be disposed at a first body location;
   a heart pacing unit adapted to be disposed at a second body location remote from said first body location and including pulse generating means for generating heart stimulating pulses at a basic pacing rate, means for wirelessly receiving said body activity signal transmitted by said at least one body activity sensor unit, and means connected to said means for wirelessly receiving for controlling said pulse generating means to vary said basic pacing rate as a function of said body activity signal;
   said heart pacing unit further including means for receiving an information signal and means for wirelessly transmitting said information signal; and
   said at least one body activity sensor unit further including means for wirelessly receiving said information signal transmitted by said heart pacing unit and means for altering the operation of said means for sensing body activity in response to said information signal.

2. A heart pacing system as claimed in claim 1, wherein said at least one body activity sensor unit and said pacing unit are contained in respective housings adapted for implantation in said body to said first and second locations respectively.

3. A pacing system as claimed in claim 1, further comprising a programmer/recorder unit adapted to be disposed outside of said body, said programmer/recorder unit including means for generating and transmitting said information signal to said heart pacing unit.

4. A body activity-controlled heart pacing system comprising:
   a plurality of body activity sensor units respectively adapted to be disposed at spaced locations within a patient's body, each body activity sensor unit including means for sensing body activity and generating a body activity signal, and means for wirelessly transmitting said body activity signal;
   a heart pacing unit including pulse generating means for generating heart stimulating pulses at a basic pacing rate, means for wirelessly receiving the body activity signals respectively transmitted by each of said body activity sensor units, and means connected to said means for wirelessly receiving for controlling said pulse generating means to vary said basic pacing rate in response to at least one of said body activity signals;
   said heart pacing unit further including means for receiving an information signal and means for wirelessly transmitting said information signal; and
   each of said body activity sensor units further including means for wirelessly receiving said information signal and altering the operation of said means for sensing body activity in response to said information signal.

5. A pacing system as claimed in claim 4, further comprising a programmer/recorder unit adapted to be disposed outside of the body of said patient, said programmer/recorder unit including means for generating said information signal and means for transmitting said information signal to said heart pacing unit.

6. A method for pacing a heart in the body of a patient comprising the steps of:
   generating heart stimulating pulses at a basic pacing rate from a pacing unit disposed at a first body location;
   sensing body activity at at least one location in the body of said patient remote from said first location;
   generating a body activity signal based on the sensed body activity in at least one body activity sensor unit disposed remote from said pacing unit;
   wirelessly transmitting said body activity signal from said at least one body activity sensor unit to said pacing unit;

wirelessly receiving said body activity signal in said pacing unit and altering said basic pending rate as a function of the received body activity signal;

entering an information signal in said pacing unit;

wirelessly transmitting said information signal from said pacing unit to said at least one body activity sensor unit; and altering the operation of said at least one body activity sensor unit based on said information signal.

7. A method as claimed in claim 6, wherein the steps of entering said information signal in said pacing unit comprise the steps of:

generating an information signal in an external unit disposed outside of the body of said patient;

transmitting said information signal from said external unit to said pacing unit; and receiving said information signal from said external unit in said pacing unit.

8. A method as claimed in claim 6, wherein the step of sensing body activity is further defined by sensing body activity at a plurality of locations in the body of said patient all remote from said first location, wherein the step of generating a body activity signal is further defined by generating a body activity signal based on the sense body activity in each of said body activity sensor units, wherein the step of wirelessly receiving body activity signal is further defined by wirelessly receiving said body activity signals in said pacing unit from each of said body activity sensor units and altering said basic pacing rate as a function of the received body activity signals, wherein the step of wirelessly transmitting said information signal is further defined by wirelessly transmitting said information signal from said pacing unit to each of said body activity sensor units, and wherein the step of altering the operation of said body activity sensor unit is further defined by altering the operation of each of said body activity sensor units based on said information signal.

* * * * *